US012785753B2

(12) United States Patent
Quint

(10) Patent No.: US 12,785,753 B2
(45) Date of Patent: Nov. 3, 2026

(54) REUSABLE COMMUNICATION DEVICE FOR A CATHETER FOR RELEASABLE CONNECTION TO A CATHETER HUB OF THE CATHETER

(71) Applicant: BIOTRONIK AG, Bülach (CH)

(72) Inventor: Bodo Quint, Dettighofen (DE)

(73) Assignee: BIOTRONIK AG, Buelach (CH)

( * ) Notice: Subject to any disclaimer, the term of this patent is extended or adjusted under 35 U.S.C. 154(b) by 562 days.

(21) Appl. No.: 18/234,184

(22) Filed: Aug. 15, 2023

(65) Prior Publication Data

US 2024/0088942 A1 Mar. 14, 2024

(30) Foreign Application Priority Data

Sep. 13, 2022 (EP) .................................... 22195290

(51) Int. Cl.
*H04B 5/73* (2024.01)
*A61M 5/168* (2006.01)
(Continued)

(52) U.S. Cl.
CPC ........... *H04B 5/73* (2024.01); *A61M 5/16881* (2013.01); *A61M 25/0097* (2013.01);
(Continued)

(58) Field of Classification Search
CPC . H04B 5/73; A61M 5/16881; A61M 25/0097; A61M 2005/1403;
(Continued)

(56) References Cited

U.S. PATENT DOCUMENTS

2011/0127951 A1* 6/2011 Walley .................... H02J 50/10
320/108
2014/0094881 A1 4/2014 Dabrowiak et al.
(Continued)

FOREIGN PATENT DOCUMENTS

WO 2022140766 A1 6/2022

OTHER PUBLICATIONS

European Search Report from the corresponding European Patent Application No. EP 22195290.6, dated Mar. 1, 2023.

*Primary Examiner* — Cindy Trandai
(74) *Attorney, Agent, or Firm* — Greer, Burns & Crain, Ltd.; Steven P. Fallon

(57) ABSTRACT

A communication device for near field communication (NFC) with a catheter includes an NFC coil and a communication circuit connected thereto and is configured for bidirectional near-field communication with the catheter. The device includes a rechargeable energy storage device, and an electric charging coil connected to a charging circuit for charging the energy storage device. A housing surrounds the NFC coil, the communication circuit, the energy storage device, the charging coil and the charging circuit. The housing is configured to be releasably secured to the catheter for near-field communication with the catheter. The housing is preferably in the form of a catheter handle. A system includes a docking station configured to communicate with and dock the communication device. The system can include a computer configured to communicate with the docking station.

15 Claims, 2 Drawing Sheets

(51) Int. Cl.
*A61M 25/00* (2006.01)
*A61M 5/14* (2006.01)

(52) U.S. Cl.
CPC ............... *A61M 2005/1403* (2013.01); *A61M 2205/3561* (2013.01); *A61M 2205/3592* (2013.01); *A61M 2205/502* (2013.01); *A61M 2205/70* (2013.01); *A61M 2205/8243* (2013.01)

(58) Field of Classification Search
CPC .. A61M 2205/3561; A61M 2205/3592; A61M 2205/502; A61M 2205/70; A61M 2205/8243; A61M 2205/3317; A61M 2205/3334; A61B 5/6853; A61B 2560/0214; A61B 2562/0247; A61B 5/0015; A61B 5/6852; H02J 50/10; H02J 50/80
See application file for complete search history.

(56) References Cited

U.S. PATENT DOCUMENTS

2016/0246265 A1* 8/2016 An .......................... H02J 50/12
2017/0163788 A1* 6/2017 Andersen ............... H04N 7/142
2018/0021099 A1* 1/2018 Warner ................... G06F 3/016
604/95.01
2020/0093998 A1* 3/2020 Benedict ............... A61F 9/0008
2020/0286070 A1 9/2020 Garrett
2021/0046277 A1* 2/2021 Samoocha .............. B08B 13/00
2021/0369283 A1* 12/2021 O'Halloran ...... A61B 17/12172
2022/0362509 A1* 11/2022 Arevalos ................ A61B 5/204
2022/0395641 A1* 12/2022 O'Hare ................... A61M 5/20

* cited by examiner

REUSABLE COMMUNICATION DEVICE FOR A CATHETER FOR RELEASABLE CONNECTION TO A CATHETER HUB OF THE CATHETER

PRIORITY CLAIM

This application claims priority under 35 U.S.C. § 119 and all applicable statutes and treaties from prior European Application No. EP 22195290.6, which was filed Sep. 13, 2022.

FIELD OF THE INVENTION

The invention relates to a communication device for a catheter for releasable mechanical connection to a catheter hub of the catheter. The invention further relates to a medical system including such a communication device.

BACKGROUND

The catheter may be, for example, a balloon catheter which is used in the context of an angioplasty to expand a stenosis by a stent which is arranged on a balloon of the balloon catheter and is transported by the balloon catheter to the target location and is expanded there by the balloon or is anchored in the vessel to eliminate the constriction. The catheter may, for example, have a sensor to determine the diameter of the balloon. Other sensors can be used, e.g. temperature or pressure sensors. Alternatively or additionally, the catheter may be used, for example, to release a medicament into the patient.

The necessary electrical functionalities of the respective catheter, however, mean that a suitable power supply and signal or data connectivity to the respective catheter must be realised.

A technique for direct connection to the catheter, however, carries the risk of restricting the tactile handling for the user as well as disadvantages with regard to the sterilisability and durability of the electrical connections.

SUMMARY OF THE INVENTION

A communication device for near-field communication with a catheter includes an electrical near field communication (NFC) coil and a communication circuit connected thereto. The communication circuit and the coil are configured for bidirectional near-field communication with the catheter (in particular with an NFC transponder of the catheter). The communication device includes a rechargeable energy storage device, and an electric charging coil connected to a charging circuit configured to charge the energy storage device. A housing encloses the NFC coil, the communication circuit, the energy storage device, the charging coil and the charging circuit. The housing is configured to be releasably secured to the catheter for near-field communication with the catheter. The housing is preferably in the form of a catheter handle. A system includes a docking station configured to communicate with and dock the communication device. The system can include a computer configured to communicate with the docking station.

BRIEF DESCRIPTION OF THE DRAWINGS

In the following, embodiments of the invention as well as further features and advantages of the invention will be explained with reference to the figures, in which.

DETAILED DESCRIPTION OF THE PREFERRED EMBODIMENTS

Figure 1:
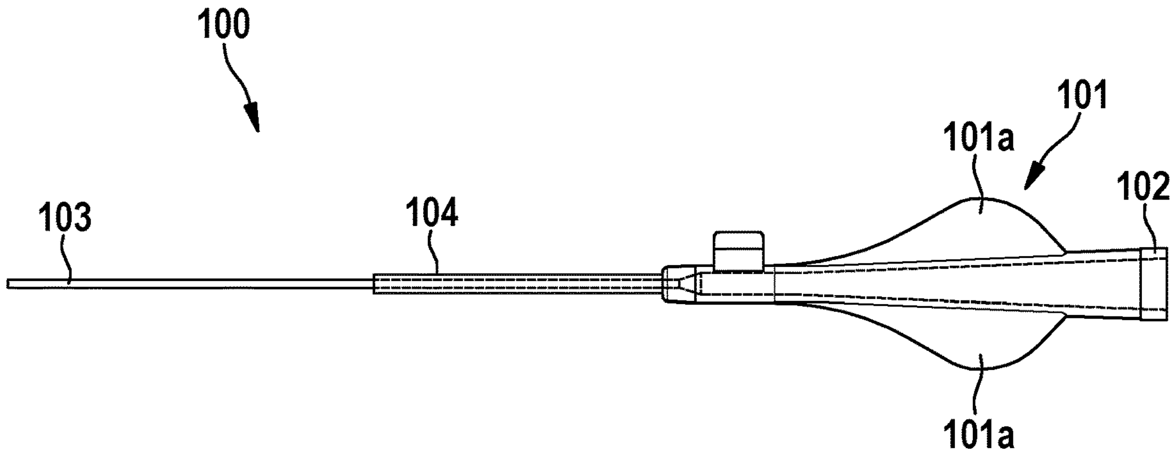
FIG. 1 shows a catheter known from the prior art.

According to one preferred embodiment, the communication device or the housing is releasably securable to a catheter hub of the catheter. The catheter hub is provided at a proximal end of the catheter and in particular has a connection, for example a Luer connector, for connecting a line via which a fluid medium is introducible into a lumen of the catheter.

The term near-field communication (NFC for short) refers on the one hand to the standard of the same name (NFC) and on the other hand to the underlying technical principle of contactless data exchange at an operating frequency of 13.56 MHz.

Near-field communication in the invention is based on communication between a reader (here including the NFC coil and the communication circuit of the communication device) and a passive NFC transponder, preferably arranged in the catheter, which draws its supply voltage from the magnetic field generated by the reader or the NFC coil. The transponder also has a conductor loop or NFC coil for interaction with or inductive coupling to the NFC coil of the communication device.

On the one hand, the inductive coupling of the reader and the transponder transmits the energy to supply the transponder, but on the other hand, data must also be exchanged between the reader and the transponder. This data transmission is specified, for example, in ISO/IEC 14443-2 for RFID systems at 13.56 MHz. As a rule, the reader and transponder communicate according to the RTF principle (RTF for Reader Talks First). In this case, communication or data transmission is initiated by the reader; the transponder only sends data in response to a corresponding signal from the reader. The data or signal is transmitted from the reader to the transponder via direct amplitude modulation of the carrier signal. By contrast, the data or signal is transmitted from the transponder to the reader by load modulation with subcarrier. In this context, load modulation means that the transponder varies its impedance in order to modulate the transmission energy with the data stream. Due to the inductive coupling of the NFC coil (reader) of the communication device with the NFC coil of the transponder of the catheter, this load variation causes current and voltage changes in the NFC coil of the communication device, which may be detected via said communication circuit.

The communication device according to the invention enables advantageous functional properties, such as simple and complete sterilisability of the system and, at the same time, assistive catheter handling, in particular due to an ergonomic shaping of the housing of the communication device.

Furthermore, the invention may be universally applied to any catheter systems and, in this context, allows the implementation of electrical catheter functions (for example balloon dilation, SDS, drainage catheter, drainage catheter with medication function, drainage catheter with time-controlled functionality, guide catheter with additional sensors), since the communication device according to the invention enables the direct transmission of energy to the catheter and its functions may be controlled via near-field communication. Furthermore, the invention thus allows a cost reduction with regard to the respective catheter.

Furthermore, the communication device according to the invention may be releasably mechanically connected to connection systems for infusion and injection devices, in particular to a Luer system, or also to devices connectable to such connection systems, for example a flow valve provided with a Luer connector, and a communicative coupling between the reader of the communication device and a transponder of the connection system or the device connectable to such a connection system for data and signal transmission may be achieved. In this way, the communication device may be used, for example, to control an infusion or injection device connected to the connection system, for example for medicament delivery via a controllable valve of an infusion device.

The NFC technology may be used particularly advantageously in conjunction with the present invention, since here energy transmission or communication takes place in a near-field range (a few mm to a few cm) via corresponding NFC coils or antennas, the range of which is completely sufficient due to the proximity between the communication device and the catheter, and at the same time has a relatively low energy consumption.

The data transmission is based on inductive coupling (see above), which is usually intended for a transmission frequency of 13.56 MHz and is advantageously small in terms of the necessary components and therefore corresponds to the dimensions realised by a typical catheter Luer or catheter hub.

The NFC communication circuit of the communication device may advantageously be configured to be programmable, not exclusively for storing data content, so that complex functional extensions may also be realised. For example, ARM processor cores with freely programmable resources may be integrated into such communication modules so that corresponding computing power is also available.

Preferably, according to one embodiment of the invention, the housing is configured to be connected to the catheter or to the catheter hub by a clamping connection. For this purpose, the housing may have latching tongues, each of which may be configured to engage behind a material region of the catheter or the catheter hub to form the releasable connection.

According to a preferred embodiment of the communication device, it is provided that the housing is formed as a handle.

Furthermore, according to one embodiment of the communication device, the housing is configured to be grasped by just one hand for handling the catheter when the housing is releasably connected to the catheter hub of the catheter.

Furthermore, according to one embodiment of the communication device, it is provided that the housing has a recess for receiving a thumb of a user (in particular a doctor) of the communication device, and/or that the housing has a recess for an index finger of a user (in particular a doctor).

Furthermore, according to one embodiment, the housing may have a recess for receiving a region of the catheter, in particular of the catheter hub.

Furthermore, according to one embodiment of the communication device, it is provided that the housing hermetically encloses said components (the NFC coil, the communication circuit, the energy storage device, the charging coil and the charging circuit as well as any further components) and in particular does not have any joints or openings. The housing may, for example, be made of a plastic, such as POM (polyoxymethylene). The housing may be formed from a resin in which said components are cast. Furthermore, the housing may be formed by overmoulding said components with the plastic.

Furthermore, according to one embodiment of the communication device, it is provided that the communication device includes a transmitting-receiving unit (i.e. a transceiver unit) configured to communicate with a docking station. The communication may take place, for example, at a transmission frequency of 433 MHz/898 MHz.

Furthermore, this communication may take place according to a WLAN standard (for example from the IEEE 802.11 family), a WPAN or Bluetooth standard or, for example, according to MICS/MEDS 400 MHz transmission standard (fda/eu).

According to one embodiment of the invention, the charging coil of the communication device is an NFC charging coil for charging the energy storage device at the docking station, the NFC charging coil being configured to also take over the communication for a monitoring and/or a system test and/or a configuration of the communication device. The charging of the energy storage device as well as said configuration are thus also preferably carried out via an inductive coupling within the scope of near-field communication (NFC).

Furthermore, according to one embodiment of the communication device, it is provided that the communication device has an optical display, in particular in the form of at least one light-emitting diode (LED), the communication device being configured to display a state of the communication device by the optical display device.

The state may be, for example, a state of charge of the energy storage device or a charging process of the energy storage device that is currently taking place. Furthermore, the state may be a communication currently taking place between the communication device and the catheter and/or between the communication device and a docking station for the communication device.

Preferably, the optical display is completely surrounded by the housing of the communication device, i.e. the housing does not have a through-opening in a housing wall of the housing for the optical display. The housing for the optical display may have a translucent or transparent region covering the optical display.

According to one embodiment of the invention, the catheter may be a drainage catheter, the communication device being configured to cause the catheter to deliver a medicament to a patient via the NFC coil of the communication unit.

In this way, medicament delivery may be initiated by the communication device and may be performed in a time-controlled fashion. The function for this may be configured during a sterilisation and/or charging process that takes place when the communication unit is docked to the docking station. The communication device may transmit a signal to the docking station indicating that the medicament is being or has been dispensed correctly.

Furthermore, according to one embodiment of the communication device, it is provided that the catheter (for example, the catheter may be a balloon catheter) includes at least one sensor, in particular a resistive or capacitive sensor, for example, a sensor for determining the diameter of a balloon of the balloon catheter, the communication device being configured to read an output signal of the at least one sensor and/or data determined therefrom by the NFC coil and the communication circuit and preferably to forward it to a docking station.

In this way, the communication device may forward the measured values obtained by the catheter to a higher-level analysis system (for example via the docking station).

Furthermore, according to one embodiment of the communication device, it is provided that the communication device is configured to read catheter-specific data, in particular the diameter of the balloon and/or calibration data of a sensor, for example a pressure sensor, from the catheter via the NFC coil.

In this respect, the communication device may be configured to forward the read, catheter-specific data to a higher-level system (for example via the docking station), so that said data may be visualised there in detail. For example, all information necessary for a catheter intervention may be displayed on a screen of the superordinate system. The specifically recorded data may thus allow both the identification/classification of the catheter as well as an additional detailing of catheter properties through, for example, catheter-specific calibration data. Furthermore, additional properties and/or instructions and/or handling recommendations and/or measurement results may also be passed on to the user of the catheter (for example by recording sensors on the catheter).

Another aspect of the invention relates to a medical system including at least one (or more) communication device(s) according to the invention and a separate docking station, wherein the at least one communication device is dockable to the docking station.

According to one embodiment of the invention, the docking station may include an input interface, for example in the form of a keyboard, for entering information or for programming the docking station or the at least one communication device.

Furthermore, according to one embodiment of the medical system, it is provided that the docking station for docking the at least one communication device has a receptacle for receiving the at least one communication device. Here, being docked means in particular that the at least one communication device is arranged in a defined position with respect to the docking station, which allows charging of the energy storage of the communication device by the docking station. This may be ensured, for example, by arranging the communication device in the assigned receptacle of the docking station.

Furthermore, according to one embodiment of the invention, it is provided that the docking station is configured to flush the at least one communication device with a solution, in particular for cleaning and/or maintenance purposes, and/or to sterilise the at least one communication device by contacting it with a sterilising agent when the at least one communication device is docked to the docking station. The sterilising agent may be present, for example, as a sterilising liquid which is introduced into the receptacle for the communication device.

Furthermore, according to one embodiment of the medical system, it is provided that the docking station is configured to charge the energy storage device of the at least one communication device via the charging coil when the at least one communication device is docked to the docking station (i.e. for example is arranged in the assigned receptacle of the docking station), and/or in that the docking station is configured to carry out a system test of the at least one communication device via the charging coil when the at least one communication device is docked to the docking station (i.e. is arranged in the assigned receptacle of the docking station, for example).

The docking station may in particular have monitoring functionalities. For example, according to one embodiment, the docking station may be configured to display a state of charge of the energy storage device to the at least one communication device. The state of charge describes the current capacity of the energy storage device in relation to the maximum capacity of the energy storage device. Furthermore, according to one embodiment, the docking station may be configured to emit a warning signal, for example if the state of charge falls below a predefined threshold value.

Furthermore, according to one embodiment of the medical system, the docking station may be configured to indicate a successful device pairing between the at least one communication device and the catheter.

Furthermore, according to one embodiment of the medical system, it is provided that the docking station is set up to configure the at least one communication device via the charging coil, so that in particular the at least one communication device, after configuration, may control a function of the catheter via the NFC coil of the at least one communication device and/or may read data from the catheter.

The configuration settings may further concern, for example, the setting of a radio channel between the docking station and the communication device or between the catheter and the communication device as well as an ID of the respective communication.

Furthermore, according to one embodiment of the medical system, it is provided that the docking station includes a transmitting-receiving unit (i.e. a transceiver unit) configured to communicate with the transceiver unit of the at least one communication device, in particular when the at least one communication device is releasably secured to the catheter hub of the catheter as intended.

Furthermore, according to one embodiment of the medical system, it is provided that the medical system has at least one computer, the docking station being configured to transmit data to the at least one computer via a data exchange connection, said data having been transmitted to the docking station by the at least one communication device. The at least one computer may be configured for further processing and/or visualisation of the transmitted data.

Furthermore, the at least one computer may be part of a computer network, in particular a server of the computer network. The computer network may be a computer network of a home monitoring service centre (HMSC), the computer network being configured to manage or monitor patient data. In this regard, the computer network or the at least one computer may be configured to link catheter-specific data to data relating to an intervention (using the catheter) and to patient data of the treated patient, in particular to generate a handling recommendation with regard to a future intervention on the same patient or another patient. The data exchange connection may use one or more connection types (for example Ethernet, WLAN, a mobile network, a network connection according to the Internet protocol, etc.).

According to one embodiment of the medical system, the at least one communication device is configured to initiate and to control a medicament release of the catheter, the docking station being configured to transmit a corresponding configuration of the at least one communication device to the at least one communication device, or to perform such a configuration, when the at least one communication device is docked to the docking station, the configuration being made, for example, during a sterilisation process and/or a charging process of the energy storage device of the at least one communication device.

Furthermore, according to one embodiment of the medical system, it is provided that the at least one communication device is configured to read an output signal of the at least one sensor and/or data determined therefrom by the NFC coil and the communication circuit of the at least one communication device and to forward it to the docking station, the docking station being configured to transmit the output signal and/or said data to the at least one computer of the medical system via the data exchange connection.

Furthermore, according to one embodiment of the medical system, it is provided that the at least one communication device is configured to read catheter-specific data from the catheter by the NFC coil and the communication circuit of the at least one communication device and to transmit said data to the docking station, the docking station being configured to transmit the catheter-specific data via the data exchange connection to the at least one computer, which is configured in particular to display the catheter-specific data and/or data generated therefrom on a screen or to process said data in another way.

The at least one computer may in particular display in detail all the information necessary for a catheter intervention on the screen. The specifically recorded data allows in particular both the identification/classification of the catheter as well as an additional detailing of catheter properties by, for example, catheter-specific calibration data.

Furthermore, according to one embodiment of the medical system, it is provided that the at least one communication device is configured to read sensor data of one or more sensors of the catheter from the catheter by the NFC coil and the communication circuit of the communication device and to transmit said data to the docking station, the docking station being configured to transmit the sensor data via the data exchange connection to the at least one computer, which is configured to use the sensor data to provide at least one of the following items of information to an operator (in particular doctor) of the catheter: at least one instruction for operating the catheter, at least one handling recommendation with regard to an intervention to be carried out by the catheter, at least one measurement result obtained using the catheter.

Furthermore, according to one embodiment of the invention, it is provided that the medical system includes the respective catheter to which the communication device is releasably, in particular clampably, securable (see above).

FIG. 1 shows a catheter 100, with a proximal end portion formed by a so-called catheter hub 101, which has a connection 102 at a proximal end for introducing a fluid medium (for example an inflation medium) into a lumen of the catheter 100, the connection 102 preferably being formed as a Luer connector. Furthermore, the catheter hub 101 has two wings 101*a* protruding in opposite directions or perpendicularly to the axial direction of the catheter 100, which provide for better handling of the catheter 100. The catheter hub 101, in particular its wings 101*a*, may be held in the hand by the doctor during insertion and placement of the catheter 100. Furthermore, the catheter 100 may include a stabiliser 104 extending from the catheter hub 101 and surrounding a proximal portion of the outer shaft 103 for stabilising the outer shaft 103.

Figure 2:
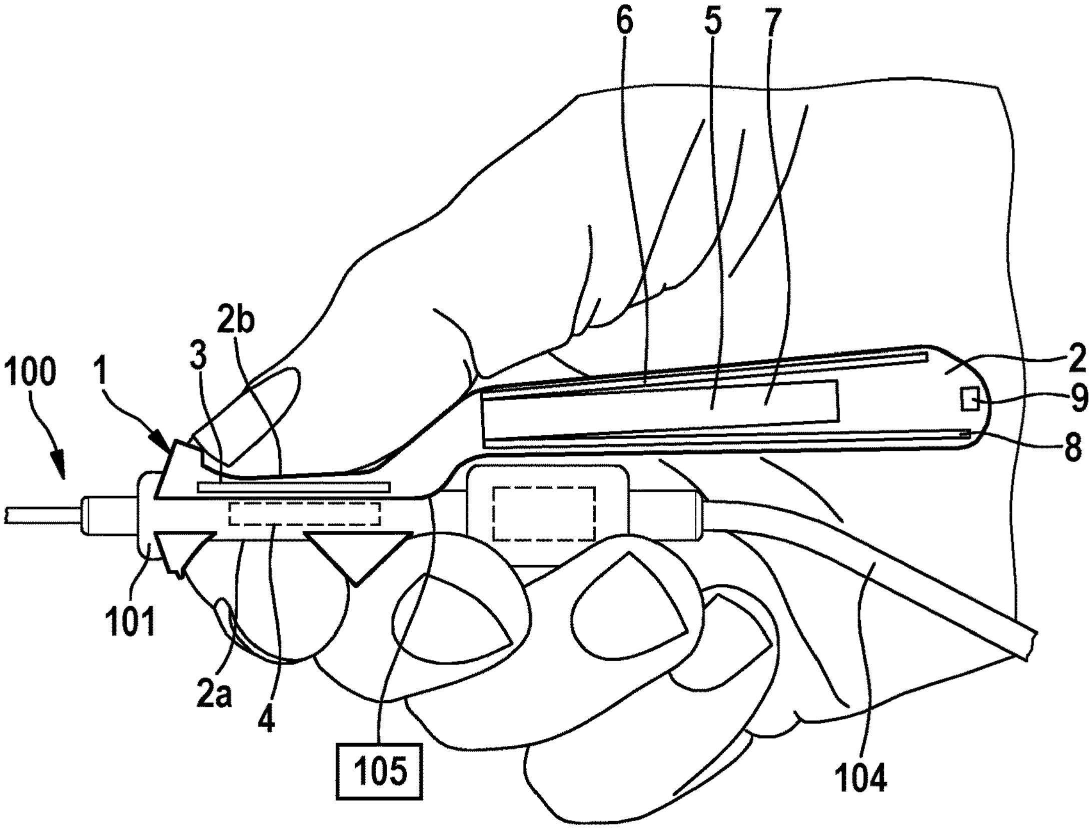
FIG. 2 shows an embodiment of a communication device according to the invention.

FIG. 2 shows an embodiment of a communication device 1 according to the invention for near-field communication N1 with a catheter, for example with a catheter 100 of the type shown in FIG. 1.

The communication device 1 has an NFC coil 3 and a communication circuit 4 connected thereto, which is configured for bidirectional near-field communication N1 with the catheter 10. For this purpose, the catheter 100 may include a corresponding transponder 105, which is simultaneously supplied with energy L1 via the NFC coil 3. Furthermore, the communication device 1 includes a rechargeable energy storage device 5 and an electrical charging coil 6, which is connected to a charging circuit 7 for charging the energy storage device 5. The charging coil 6 is preferably an NFC coil 6, so that charging of the energy storage device may be performed via inductive coupling. The communication device 1 further includes a housing 2 surrounding the NFC coil 3, the communication circuit 4, the energy storage device 5, the charging coil 6 and the charging circuit 7, the housing 2 being configured to be releasably secured to the catheter 10 for near-field communication with the catheter 10. Here, the housing 2 is preferably formed as a catheter handle, which may have ergonomic recesses 2*a*, 2*b* for the index finger and thumb of the operator (compare FIG. 1). In contrast to FIG. 1, FIG. 2 also shows a line 104 connected to the Luer connector 102 for introducing a fluid medium into the lumen of the catheter 100.

The communication device 1 further preferably includes a transceiver unit 8, which is configured for wireless communication F between the communication device 1 and a further device (for example a docking station 21, see below). The transceiver unit 8 may, for example, be based on a WLAN or Bluetooth standard or other transmission frequencies, such as 433 MHz/898 MHz.

Furthermore, the communication device 1 preferably includes an optical display 9 for visualising a status of the communication device 1. The optical indicator 9 may have one or more light sources, such as one or more LEDs.

The housing 2 of the communication device 1 is preferably configured to hermetically enclose the components described above. The housing 2 may be formed, for example, as an overmoulding of said components with a plastic (for example POM) or by casting the components with a resin.

In this case, the optical display 9 is preferably completely surrounded by the housing 2 of the communication device 1, i.e. the housing 2 does not have any through-opening in a housing wall of the housing 2 for the optical display 9. The housing 2 for the optical display 9 may have a translucent or transparent region covering the optical display 9 or may be completely translucent or transparent.

Preferably, the housing 2 of the communication device 1 is configured to be releasably connected to the catheter 100 or to the catheter hub 101 by a clamping connection. In this embodiment, the housing 2 is shaped in such a way that it may be clamped onto the catheter 10, in particular onto the catheter hub 101, and is thus releasably connected to the catheter 10.

Figure 3:
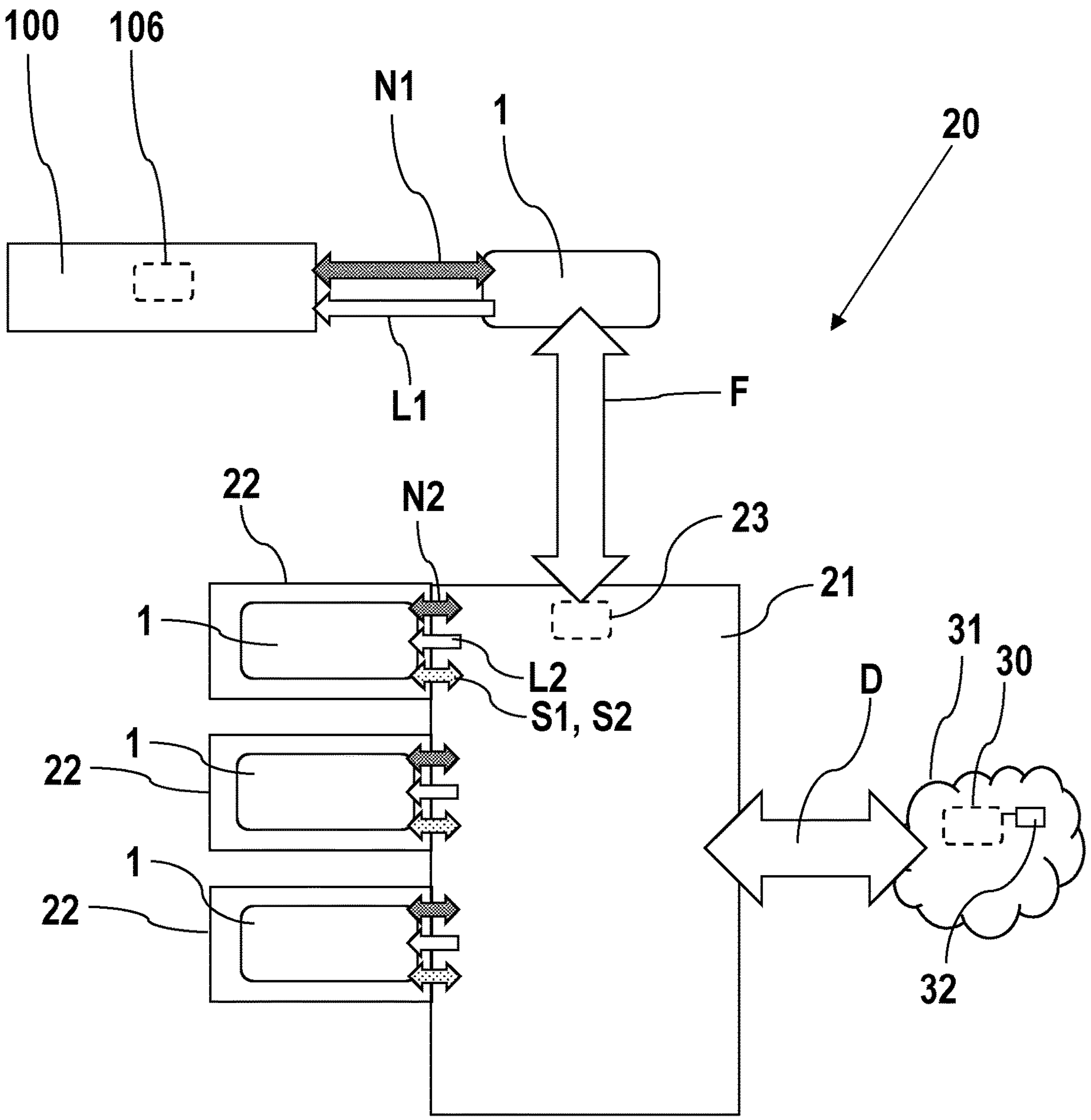
FIG. 3 shows an embodiment of a system according to the invention with a communication device of the type shown in FIG. 2 as well as a docking station and a catheter.

FIG. 3 illustrates a possible embedding of a communication device 1 according to the invention in a medical system 20, which may also include the catheter 100 to which the communication device 1 is releasably connectable.

The medical system 20, further includes a docking station 21, wherein the at least one communication device 1 is dockable to the docking station 21.

According to one embodiment, the system 20 may include a plurality of communication devices 1 according to the invention, which may each be docked to the docking station 21, in particular simultaneously. The communication devices 1 may also have different functions with regard to the catheter 100 or with regard to different catheters or may be configured according to different embodiments described herein.

For docking the at least one or the respective communication device 1, the docking station 21 preferably includes a receptacle 22 assigned to the communication device 1 for receiving the communication device 1.

Preferably, the docking station 21 is configured to flush the docked communication device 1 or the communication device 1 arranged in the corresponding receptacle 22 with a solution S1 and/or to sterilise the communication device 1 by contacting it with a sterilising agent S2. The solution S1 or the sterilising agent S2 may be introduced here into the respective receptacle 22, and removed from it again, through the docking station 21.

The docking station 21 is furthermore preferably configured to charge the energy storage device 5 of the respective communication device 1 via the charging coil 6 of the communication device 1 (L2) when the communication device 1 is docked to the docking station 21. In this case, the docking station 21 may also perform a system test of the communication device 1 via its charging coil 6.

Furthermore, the docking station 21 is preferably set up to configure the respective communication device 1 via the charging coil 6 of the respective communication device 1 by near-field communication N2, so that in particular a communication device 1, after configuration, may control a function of the catheter 100 with which the communication device 1 is paired via the NFC coil 3 of the communication device 1 and/or may read data from the catheter 100.

For wireless communication of the docking station 21 with a communication device 1 releasably secured to the catheter 100, the docking station 21 preferably includes a transceiver unit 23 configured for wireless communication F with the transceiver unit 8 of the communication device 1.

Furthermore, the medical system 20 may include at least one computer 30, wherein the docking station 21 is configured to transmit data to the at least one computer 30 via a data exchange connection D, said data having been transmitted to the docking station 21 by the at least one communication device 1 (for example via near-field communication N1 in the docked state or via the transceiver units 8, 23).

According to one embodiment, the at least one communication device 1 is configured to read catheter-specific data from the catheter 100 by its NFC coil 3 and the communication circuit 4 and to transmit said data to the docking station 21 (for example via near-field communication N1 in the docked state or via the transceiver units 8, 23), the docking station 21 preferably being configured to transmit the catheter-specific data via the data exchange connection D to the at least one computer 30, which is preferably configured to display the catheter-specific data and/or data generated therefrom on a screen 32. The at least one computer 30 may be part of a computer network 31, in particular a server 30 of the computer network 31. The computer network 31 may be a computer network 31 of a home monitoring service centre (HMSC), the computer network 31 being configurable to manage patient data and, in particular, to automatically establish a link between catheter-specific data and data of an intervention (using the catheter 100) and patient data of the treated patient, in particular to generate a handling recommendation with regard to a future intervention on the same patient or on another patient.

In particular, the communication device 1 according to the invention allows a decentralised monitoring of functions of a catheter 100. For example, according to one embodiment, the communication device may initiate a medicament release by the catheter 100 (for example appropriately equipped drainage catheter) and may perform said release in a time-controlled fashion by the catheter 100. The function for this may be configured for example during the sterilisation and charging process of the energy storage device 5 (see above), with a feedback to the docking station 21 regarding a correct execution of the medicament release being possible.

Furthermore, a communication device 1 according to the invention advantageously allows a functional catheter sensor system to be provided for a higher-level analysis system (for example in the form of the at least one computer 30 or computer network 31 and any components connected thereto). For example, the communication device 1 may be configured to connect a resistive or capacitive catheter sensor system to the higher-level analysis system and to supply the latter with corresponding sensor data.

Furthermore, a communication device 1 according to the invention advantageously allows catheter-specific data to be read from the catheter 100, a higher-level system, for example the at least one computer 30 or the computer network 31, visualising in detail all the information required for the catheter intervention on a screen 32. The specifically recorded data allows both the identification/classification of the catheter 100 as well as an additional detailing of catheter properties by, for example, catheter-specific calibration data.

Furthermore, additional properties, instructions, handling recommendations and/or measurement results may be passed on to the user by recording sensors on the catheter 100.

The communication device 1 according to the invention advantageously has the capabilities to supply a medical device (for example a catheter 100) with electrical energy and to provide a communication and monitoring functionality for the medical device. The design according to the invention thereby supports a complete sterilizability on site, and can also support a time-controlled monitoring or activation function on this catheter system.

The invention claimed is:

1. A medical system comprising at least one communication device for near-field communication with a catheter, the communication device comprising: an NFC (near-field communication) coil and a communication circuit connected thereto, the NFC coil and communication circuit being configured for bidirectional near-field communication with the catheter through the NFC coil; a rechargeable energy storage device; an electric charging coil connected to a charging circuit configured to charge the rechargeable energy storage device; and a housing surrounding the NFC coil, the communication circuit, the rechargeable energy storage device, the charging coil, wherein the housing is formed as a catheter handle; a docking station, wherein the at least one communication device is configured to dock to the docking station; and at least one computer, the docking station being configured to transmit data received from the at least one communication device to the at least one computer via a data exchange connection.

2. The medical system according to claim 1, wherein the communication device comprises a transceiver unit configured for wireless communication with the docking station.

3. The medical system according to claim 1, wherein the communication device comprises an optical display configured to display a state of the communication device.

4. The medical system according to claim 1, wherein the catheter comprises a controllable infusion valve and the communication device is configured to initiate delivery of a medicament from the infusion valve.

5. The medical system according to claim 1, wherein the catheter comprises at least one sensor configured to be wirelessly read by the communication device.

6. The medical system according to claim 1, wherein the communication device is configured to read catheter-specific data from the catheter.

7. The medical system according to claim 1, wherein the docking station comprises a receptacle configured to receive the at least one communication device.

8. The medical system according to claim 1, wherein the docking station is configured to flush the at least one communication device with a solution.

9. The medical system according to claim 1, wherein the docking station is configured to sterilise the at least one communication device when the at least one communication device is docked to the docking station.

10. The medical system according to claim 1, wherein the docking station is configured to charge the energy storage device via the charging coil when the at least one communication device is docked to the docking station.

11. The medical system according to claim 1, wherein the docking station is configured to carry out a system test of the at least one communication device via the charging coil when the at least one communication device is docked to the docking station.

12. The medical system according to claim 1, wherein the docking station is set up to configure the at least one communication device to control a function of the catheter and/or to read data from the catheter.

13. The medical system according to claim 1, wherein the docking station comprises a transceiver unit configured to communicate with the at least one communication device when the at least one communication device is releasably secured to the catheter.

14. The medical system according to claim 1, wherein the at least one communication device is configured to read catheter-specific data from the catheter, to transmit said catheter-specific data to the docking station, the docking station being configured to transmit the catheter-specific data via the data exchange connection to the at least one computer.

15. The medical system according to claim 14, wherein the at least one computer is configured to display the catheter-specific data and/or data generated therefrom on a screen.

* * * * *